(12) United States Patent
Chen et al.

(10) Patent No.: US 11,759,597 B2
(45) Date of Patent: Sep. 19, 2023

(54) DEVICE FOR PROVIDING THERAPEUTIC GAS

(71) Applicant: BIOCREDE INC., Monrovia, CA (US)

(72) Inventors: Hao Chen, Monrovia, CA (US); Kenneth Kwun Yin Ho, Monrovia, CA (US)

(73) Assignee: BIOCREDE INC., Monrovia, CA (US)

( * ) Notice: Subject to any disclaimer, the term of this patent is extended or adjusted under 35 U.S.C. 154(b) by 0 days.

(21) Appl. No.: 17/927,211

(22) PCT Filed: Jun. 6, 2021

(86) PCT No.: PCT/US2021/036064
§ 371 (c)(1),
(2) Date: Nov. 22, 2022

(87) PCT Pub. No.: WO2021/252305
PCT Pub. Date: Dec. 16, 2021

(65) Prior Publication Data
US 2023/0181862 A1      Jun. 15, 2023

Related U.S. Application Data

(60) Provisional application No. 63/035,799, filed on Jun. 7, 2020.

(51) Int. Cl.
*A61M 16/12* (2006.01)
(52) U.S. Cl.
CPC ........ *A61M 16/12* (2013.01); *A61L 2300/114* (2013.01); *A61L 2300/602* (2013.01); *A61M 2202/0275* (2013.01)

(58) Field of Classification Search
CPC .......... A61M 16/12; A61M 2202/0275; A61L 2300/114; A61L 2300/602; A61L 2300/608; A61L 15/44; A61K 9/7084; A61K 33/00; A61F 2013/00646; A61F 13/00063
USPC ................................................... 128/203.12
See application file for complete search history.

(56) References Cited

U.S. PATENT DOCUMENTS

| 5,814,031 A * | 9/1998 | Mooney | A61L 15/44 604/304 |
| 6,599,525 B2 * | 7/2003 | Scamilla Aledo | B32B 27/12 424/443 |
| 6,893,655 B2 * | 5/2005 | Flanigan | A61K 31/465 424/443 |

(Continued)

*Primary Examiner* — Andrew J Mensh
(74) *Attorney, Agent, or Firm* — CP LAW GROUP PC; Cy Bates

(57) ABSTRACT

The disclosure concerns various devices implemented to provide a therapeutic gas rich environment to promote healing, reduce fibrosis and scar formations while maintaining anti-inflammatory, anti-thrombotic, antimicrobial, and vasodilating properties. The device generally includes a gas-donor composition that is embedded within a fibrous holding layer. Coupled to one side of the fibrous holding layer is a water-permeable layer and coupled to an opposite side of the fibrous holding layer is a gas-permeable layer. The water-permeable layer is configured to receive and communicate water to the gas-donor composition, wherein upon contact with the water, the gas-donor composition is configured to deliver a therapeutic gas through the gas-permeable layer to a treatment site of a subject.

18 Claims, 6 Drawing Sheets

(56) References Cited

U.S. PATENT DOCUMENTS

| | | | | |
|---|---|---|---|---|
| 8,790,689 | B2* | 7/2014 | Howard | A61K 31/485 |
| | | | | 424/443 |
| 9,592,161 | B2* | 3/2017 | Rule | A61F 13/0283 |
| 9,801,902 | B2 | 10/2017 | Smith | |
| 11,337,940 | B2* | 5/2022 | Andrews | A61K 31/155 |
| 2004/0241214 | A1* | 12/2004 | Kirkwood | A61F 13/0213 |
| | | | | 424/445 |
| 2013/0289471 | A1 | 10/2013 | Ward | |
| 2015/0297782 | A1 | 10/2015 | Miller | |
| 2019/0328926 | A1* | 10/2019 | Dybe | A61L 15/42 |

* cited by examiner

DEVICE FOR PROVIDING THERAPEUTIC GAS

CROSS-REFERENCE TO RELATED APPLICATIONS

This application claims benefit of priority with U.S. Provisional Application Ser. No. 63/035,799, filed Jun. 7, 2020, titled "NITRIC OXIDE RELEASING DEVICE"; the entire contents of which are hereby incorporated by reference.

TECHNICAL FIELD

This invention relates to devices for cosmetic and medical applications; and more particularly, to such devices for providing therapeutic gas to a subject at a treatment site, and methods for making the same.

BACKGROUND ART

Therapeutic gases, such as nitric oxide (NO), have been demonstrated to promote healing, reduce fibrosis and scar formations while maintaining anti-inflammatory, anti-thrombotic, antimicrobial, and/or vasodilating properties. NO serves a critical role as signaling molecule and is produced endogenously in localized concentrations by nearly every type of tissue, including endothelial cells, neural cells, and macrophages. Medical research continues to unveil an expanding range of therapeutic applications for NO, and materials research has focused toward developing and implementing NO release for skin surfaces having acne, skin blemishes, burns, or the like. Systemic exogenous delivery can be achieved through administration of organic nitrite precursors (e.g. nitroglycerine tablets, ointments, intravenous suspensions, and transdermal wound dressings). While the human body rapidly converts nitroglycerin into NO, enzyme and co-factor pathways required to activate these nitrate compounds are rapidly exhausted, resulting in drug tolerance complications. Furthermore, maintaining systemic NO delivery can result in serious physiological complications such as hypotension and free radical cell damage. Therefore, localized or site-specific delivery of the therapeutic gas has been the subject of focus and research.

Other therapeutic gases, such as $O_2$, $CO_2$, $H_2S$, $H_2$ and CO have also been shown to have physiological benefits to a subject. Oxygen facilitates fibroblast proliferation, angiogenesis, collagen synthesis and re-epithelialization. $O_2$ is an important gas that the human body needs to function, and when used at high pressure, it can be used to treat wounds and serious infections. Carbon dioxide is also an important gas for normal functioning of the human body. $CO_2$ regulates cellular respiration, maintains homeostasis and acid-base equilibrium, and regulates angiogenesis and immunity. $CO_2$ also promotes healing and is shown clinically to rejuvenate, restore and recondition the skin by accelerating the elimination of toxins, repair and neo-angiogenesis. Hydrogen sulfide, carbon monoxide and nitric oxide are the endogenous signaling gasotransmitters. Hydrogen sulfide has been shown to attenuate inflammation and increase angiogenesis. Hydrogen functions is an anti-inflammatory and anti-apoptotic agent. It also stimulates energy metabolism. Carbon monoxide plays a key role in various inflammatory and cardiovascular events. CO has been shown to have additional vasodilatory effects similar to NO.

Devices which presently exist to deliver a therapeutic gas to a targeted site have a myriad of limitations and deficiencies including, inter alia, treatment duration, ease of use, and safety.

SUMMARY OF INVENTION

Technical Problem

Conventional devices include various pads and patches. There is a need for products and methods that efficiently deliver and sustain a useful and localized dose of a therapeutic gas over a treatment duration. The conventional devices and methods which attempt to implement such a sustained therapeutic gas-rich environment for anti-microbial and anti-inflammatory purposes have remained inadequate and presently continue to fail in achieving a therapeutically acceptable standard.

Solution to Problem

Generally, a device is proposed that is configured to receive water and activate a gas-donor composition contained therein, wherein the gas-donor composition is configured to release a therapeutic gas upon contact with the water. The device comprises a fibrous holding layer disposed between a water-permeable layer and a gas-permeable layer. The gas-donor composition is configured to receive water entering the device through the water-permeable layer and deliver a therapeutic gas through the gas-permeable layer to an adjacent treatment site.

The device may comprise, for example and without limitation, a patch, pad or bandage. The device may be used for cosmetic applications, such as acne treatment or other cosmetic skin treatments. Alternatively, the device may be used for medical applications, such as wound healing and other medical applications.

In some embodiments, the device may further comprise one or more apertures adapted to allow expulsion of byproducts, including fluid byproducts, solid byproducts, excess water, tissue fluids, and biological waste expelled by the tissue cells, herein termed "exudate".

Therapeutic gas may be one selected from: NO, $O_2$, $CO_2$, $H_2S$, $H_2$, or CO. Gas-donor compositions configured to release the therapeutic gas may any known composition for releasing these gases upon contact with water and would be appreciated by one having skill in the art.

Exemplary gas-donor compositions configured to release NO may comprise: diazeniumdiolated diamine, S-nitroso-albumin, S-nitroso-N penicillamine (SNAP), S-nistrosocystine (CysNO), S-nitrosoglutathione (GSNO), diazeniumdiolated dibutylhexyldiamine (DBHD N2O2), Diethylenetriamine/NO adduct (DEAT/NO), Diethylamine NONOate (DEA/NO), Dipropylenetriamine NONOate (DPTA/NO), 6-(2-Hydroxy-1-methyl-2-nitrosohydrazino)-N-methyl-1-hexanamine (MAHMA/NO), S-nitroso-N-acetylpenicillamine, a polymer possessing an appended SNAP species, or a combination thereof.

The fibrous holding layer may comprise a woven material, fabric, paper, rope or combination or other material appreciated by one with skill in the art for achieving the purpose of embedding a gas-donor composition within a volume thereof. Example materials from which the fibrous holding layer may be manufactured include any of: cellulose, polyglucose, polyacrylonitrile, polykeratin, polydimethylsiloxane, polyester, polyurethane, polyfibrin, polypara-phenylene terephthalamide, cotton, flax, hemp, polyacrylonitrile, or a combination thereof.

The gas-permeable layer can be formed from any material that is permeable to the selected treatment gas emitted form the gas-donor composition. For example, the gas-permeable layer may be selected from: a polymer, hydrophilic material, cellulose, polyglucose, polyacrylonitrile, polykeratin, polydimethylsiloxane, polyester, polyurethane, polyfibrin, xerogel, silicone, alginate, collagen, foams, hydrocolloid, hydrogels, polyglucose, lauryl polyglucose, polydimethylsiloxane, polyacrylonitrile, polykeratin, siloxane, poly(lactic-co-glycolic acid), neoprene, sorbothane, polychloroprene, polyamide, polyimide, polyethylene glycol, polypropylene oxide, polymethlyacrylate, polyvinyl, polydextrin, alginate, polyisobutylene tackifiers, carboxymethyl cellulose, alginate, gelatin, agarose, polyolefin copolymer, polyether block amide, polyethylene, Nylon, polyethylene terephthalate, or a combination thereof. Any material permeable to the selected treatment gas associated with the device can be utilized.

The water-permeable layer may comprise any material so long as the water-permeable layer is permeable to water for promoting water-contact with the fibrous holding layer. In some embodiments, the water-permeable layer may comprise a material that is impermeable to water, but that comprises one or more perforations (openings) for permitting communication of water therethrough. In some example, the water-permeable layer may comprise: a polymer, hydrophilic material, cellulose, polyglucose, polyacrylonitrile, polykeratin, polydimethylsiloxane, polyester, polyurethane, polyfibrin, xerogel, silicone, alginate, collagen, foams, hydrocolloid, hydrogels, polyglucose, lauryl polyglucose, polydimethylsiloxane, polyacrylate, polyacrylonitrile, polykeratin, siloxane, poly(lactic-co-glycolic acid), neoprene, sorbothane, polychloroprene, polyamide, polyimide, polyethylene glycol, polypropylene oxide, polymethlyacrylate, polyvinyl, polydextrin, alginate, polyisobutylene tackifiers, carboxymethyl cellulose, alginate, gelatin, agarose, polyolefin copolymer, polyether block amide, polyethylene, Nylon, polyethylene terephthalate, or a combination thereof.

While the desired level of therapeutic gas delivered to the treatment site will be dependent on the selected therapeutic gas, the type of device, and the specific application, the desired level of a therapeutic gas like nitric oxide will be generally on the order of 0.1-8.0 Flux Units, wherein a NO Flux Unit (nitric oxide) is defined as $1.0 \times 10^{-10}$ mol cm$^{-2}$ min$^{-1}$.

Advantageous Effects of Invention

By embedding a gas-donor composition within a fibrous holding layer, and coupling a gas-permeable layer and water-permeable layer to either side of the fibrous holding layer, the invention achieves an improvement over conventional devices, namely, the ability to provide a sustained therapeutic rich environment at a treatment site for a duration for which the device is intended for use, thereby achieving physiological benefits such as reduction of fibrosis and scar formations while maintaining anti-inflammatory, anti-thrombotic, antimicrobial, and vasodilating properties. Furthermore, the device may further comprise features that allow for ease of use and safety to both the subject being treated and the surrounding environment.

DESCRIPTION OF EMBODIMENTS

Figure 1:
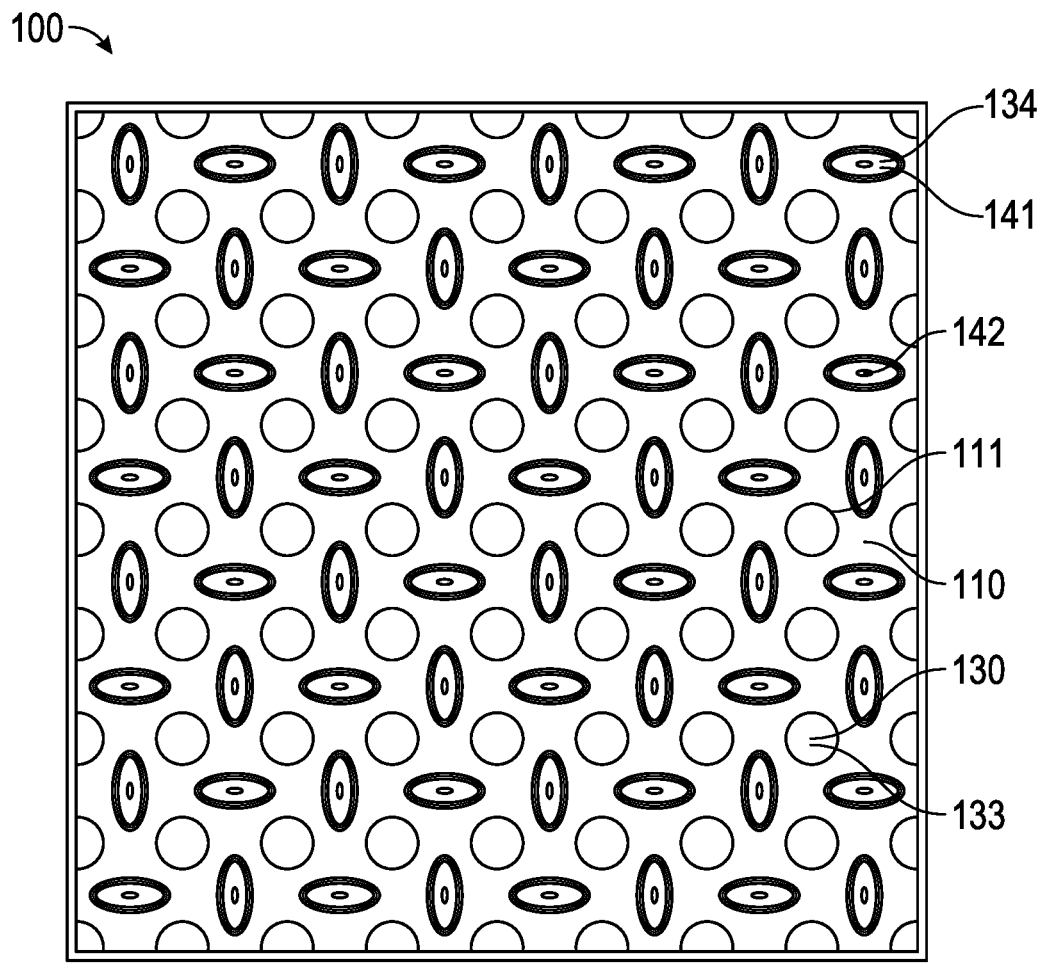
FIG. 1 shows a top view of a device in accordance with a first illustrated embodiment.

In the following description, for purposes of explanation and not limitation, details and descriptions are set forth in order to provide a thorough understanding of various embodiments of the invention. However, it will be apparent to one skilled in the art that the invention may be practiced in other embodiments, including certain variations or alternative combinations that depart from these details and descriptions. As such, this disclosure is not intended to be limiting with respect to the spirit and scope of the invention as-claimed.

In one embodiment a device for providing therapeutic gas to a subject at a treatment site is disclosed. The device comprises a water-permeable layer, a gas-permeable layer, and a fibrous holding layer disposed between each of the water-permeable layer and the gas-permeable layer. The fibrous holding layer comprises a gas-donor composition embedded therein, wherein the gas-donor composition is one that emits therapeutic gas upon contact with water, and the device is adapted to direct the therapeutic gas emitted therefrom toward the treatment site.

Generally, each of the water-permeable layer and the gas-permeable layer may further comprise a bonding layer on a surface thereof.

In some embodiments, the fibrous holding layer may comprise a plurality of holes, and the water-permeable layer and the gas-permeable layer may bond together at a periphery of each of the plurality of holes, for example by the bonding layer (adhesive), to form a plurality of overlapping junctions.

In some embodiments, one or more of the plurality of overlapping junctions may comprise an aperture extending therethrough, the aperture configured to communicate exudate from the treatment site during use.

Each of the plurality of holes and corresponding overlapping junctions may comprise an oval-shape. In some embodiments, one or more of the plurality of oval-shaped junctions may be independently oriented perpendicular with an adjacent overlapping junction, forming a pattern of orthogonal overlapping junctions.

In some embodiments, the water-permeable layer may comprise a plurality of perforations. In other embodiments, the water-permeable layer comprises no perforations and instead comprises a material which is configured to allow water to permeate therethrough. Water-permeable films and materials are well known in the art, of which, any can be employed for making the device.

The water-permeable layer may comprise, for example and without limitation: a polymer, hydrophilic material, cellulose, polyglucose, polyacrylonitrile, polykeratin, poly dimethylsiloxane, polyester, polyurethane, polyfibrin, xerogel, silicone, alginate, collagen, foams, hydrocolloid, hydrogels, polyglucose, lauryl polyglucose, polydimethylsiloxane, polyacrylate, polyacrylonitrile, polykeratin, siloxane, poly(lactic-co-glycolic acid), neoprene, sorbothane, polychloroprene, polyamide, polyimide, polyethylene glycol, polypropylene oxide, polymethlyacrylate, polyvinyl, polydextrin, alginate, polyisobutylene tackifiers, carboxymethyl cellulose, alginate, gelatin, agarose, polyolefin copolymer, polyether block amide, polyethylene, Nylon, polyethylene terephthalate, or a combination thereof. The primary purpose of the water-permeable layer is to permit communication of water through the water-permeable layer to the fibrous holding layer for activation of the gas-donor material. The water-permeable layer is generally sealed in package or by film prior to use, and is generally opened and exposed during treatment.

The fibrous holding layer may comprise, for example and without limitation: cellulose, fabric, polyglucose, polyacrylonitrile, polykeratin, polydimethylsiloxane, polyester, polyurethane, polyfibrin, poly-para-phenylene terephthalamide, cotton, flax, hemp, polyacrylonitrile, or a combination thereof and the gas-donor composition embedded therein. A primary purpose of the fibrous holding layer is to receive and hold a substantially evenly dispersed gas-donor composition therein. Other purposes may include features such as bendability and shape-forming properties. Accordingly, any material capable of holding a gas-donor material may be selected according to the knowledge and skill of one with skill in the art. In many embodiments, paper, gauze, and similar materials may be preferred.

The gas-donor composition will be one that is selected for emitting a desired treatment gas. For example and without limitation, the gas-donor composition may be selected from the group consisting of: diazeniumdiolated diamine, S-nitroso-albumin, S-nitroso-N penicillamine (SNAP), S-nistrosocystine (CysNO), S-nitrosoglutathione (GSNO), diazeniumdiolated dibutylhexyldiamine (DBHD N2O2), Diethylenetriamine/NO adduct (DEAT/NO), Diethylamine NONOate (DEA/NO), Dipropylenetriamine NONOate (DPTA/NO), 6-(2-Hydroxy-1-methyl-2-nitrosohydrazino)-N-methyl-1-hexanamine (MAHMA/NO), S-nitroso-N-acetylpenicillamine, a polymer possessing an appended SNAP species, or a combination thereof.

In some embodiments, the therapeutic gas may comprise NO, $O_2$, $CO_2$, $H_2S$, $H_2$, or CO.

The gas-permeable layer may comprise: a polymer, hydrophilic material, cellulose, polyglucose, polyacrylonitrile, polykeratin, polydimethylsiloxane, polyester, polyurethane, polyfibrin, xerogel, silicone, alginate, collagen, foams, hydrocolloid, hydrogels, polyglucose, lauryl polyglucose, polydimethylsiloxane, polyacrylonitrile, polykeratin, siloxane, poly(lactic-co-glycolic acid), neoprene, sorbothane, polychloroprene, polyamide, polyimide, polyethylene glycol, polypropylene oxide, polymethlyacrylate, polyvinyl, polydextrin, alginate, polyisobutylene tackifiers, carboxymethyl cellulose, alginate, gelatin, agarose, polyolefin copolymer, polyether block amide, polyethylene, Nylon, polyethylene terephthalate or a combination thereof. A purpose of the gas-permeable layer is to promote communication of the treatment gas that is derived from the gas-donor composition to the adjacent treatment site. Those with skill in the art can readily appreciate materials, such as films and coatings, that can be employed at the device for this purpose.

In some embodiments, the device may further comprise one or a plurality of scavengers embedded in the fibrous holding layer, each of the scavengers being adapted to capture and remove gas byproducts. Sometimes undesirable byproducts may result from the gas-donor composition. In these situations, a scavenger can be provided within or adjacent to the fibrous holding layer for arresting these undesirable byproducts, for example, toxic substances.

In some embodiments, the device may be configured to receive water from an external source, such as a spray bottle, a damp towel, or moisture from the air. In other embodiments, the water-permeable layer may comprise a blister-container. The blister-container may comprise an outer layer and an inner layer sealed at a periphery thereof and encapsulating a volume of water therein. The outer layer is configured with one or more puncture elements for puncturing the inner layer upon receiving a puncturing force and for releasing the volume of water therethrough. The water then contacts the gas-donor composition within the fibrous holding layer and causes production of the treatment gas, which proceeds through the gas-permeable layer to treat the adjacent treatment site.

In one aspect, a method of making a device for providing therapeutic gas to a subject at a treatment site is disclosed. The method comprises: dissolving a therapeutic gas donor material in a solvent to form a solution, soaking a fibrous holding layer in the solution, evaporating the solvent from the fibrous holding layer to leave the therapeutic gas donor material embedded therein, cutting a plurality of holes in the fibrous holding layer, applying a water-permeable layer to the fibrous holding layer at a first side thereof, applying a gas-permeable layer to the fibrous holding layer at a second side thereof opposite the first side, applying a force to sandwich the combination of said layers, the force creating overlapping junctions where the water-permeable layer and the gas-permeable layer meet at the holes of the fibrous holding layer, and cutting a plurality of apertures, each of the plurality of apertures being independently disposed at one of the overlapping junctions.

The method may further include wherein said cutting the holes or cutting the apertures is performed using a laser cutting instrument.

In some embodiments the solvent comprises an alcohol.

In some embodiments, the method may further comprise cutting perforations in the water-permeable layer.

Example 1—First Illustrated Embodiment

Now turning the drawings, FIG. 1 shows a top view of a device (100) in accordance with a first illustrated embodiment. The device is a pad for providing a therapeutic gas to a subject at a treatment site. The device comprises a water-permeable layer (110) coupled to a fibrous holding layer (130). The fibrous holding layer includes a gas-donor composition (133) embedded therein, and further comprises a plurality of holes (134). The water-permeable layer is coupled to the fibrous holding layer by a bonding layer (not shown) disposed therebetween. The bonding layer can comprise an adhesive. Coupled on a side of the fibrous holding layer opposite to the water-permeable layer is a gas-permeable layer (not shown). The gas-permeable layer is also coupled to the fibrous holding layer by a bonding layer disposed therebetween. Again, the boding layers may comprise any adhesive acceptable for the intended application. At each of the plurality of holes extending through the fibrous holding layer, the water-permeable layer and the gas-permeable layer meet, and are coupled to form an overlapping junction (141). Each of the overlapping junctions couples the water-permeable layer and gas-permeable layer together by the bonding layers disposed therebetween. As shown, both the plurality of holes and overlapping junctions comprise an oval-shape. Other shapes can also be utilized including triangular, circular, or rectangular or other shape. An aperture (142) extends through each of the overlapping junctions at said plurality of holes, and each aperture is configured to promote expulsion of exudate.

In this embodiment as illustrated, the water-permeable layer (110) comprises a plurality of perforations (111), each perforation is configured to allow water to pass through and contact the fibrous holding layer (130) for activation of the gas-donor composition (133). Upon activation, the gas-donor composition is configured to release the therapeutic gas, which passes through the gas-permeable layer to the adjacent treatment site.

The plurality of holes (134) is shown comprising an array configuration. The array is configured such that each hole of the plurality of holes is oriented perpendicular with any of the plurality of holes adjacent therewith. Any pattern may be employed. Such a pattern provides an ability to cut the device to any shape without losing congruity.

Figure 2:
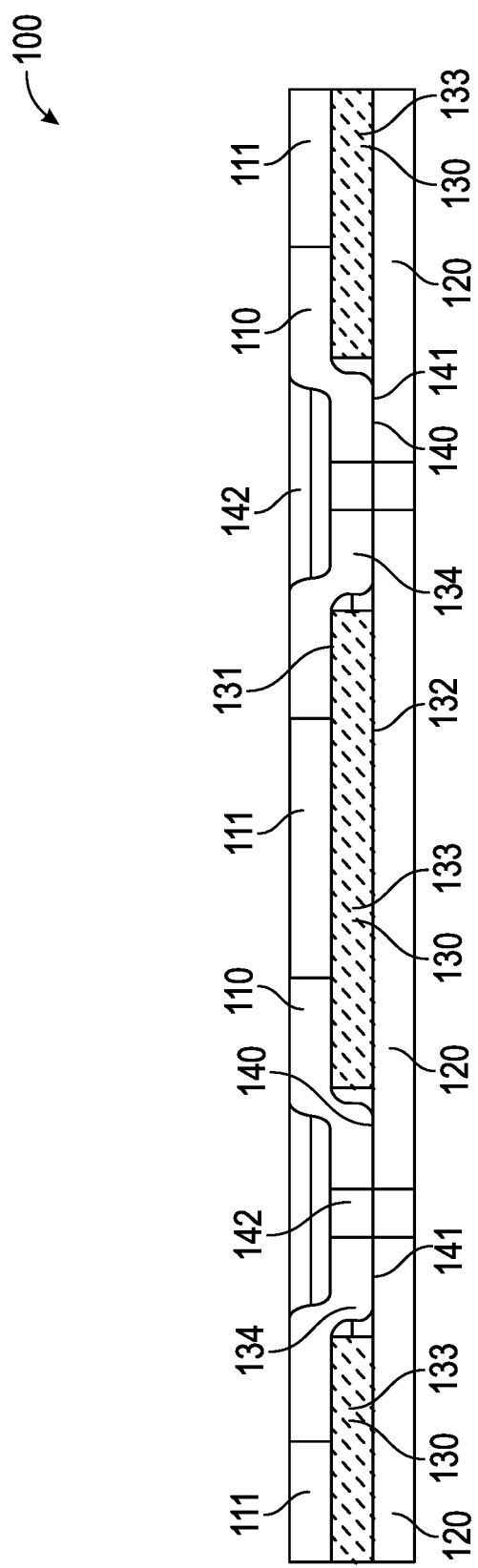
FIG. 2 shows a cross-sectional side view of the device according to the first illustrated embodiment.

FIG. 2 shows a cross-sectional side view of the device (100) according to the first illustrated embodiment. The device comprises a fibrous holding layer (130) having a first side (131) and a second side (132) opposite the first side. A water-permeable layer (110) is coupled to the first side and a gas-permeable layer (120) is coupled to the second side. Both the water-permeable layer and gas-permeable layer are coupled to the fibrous holding layer by a bonding layer (140) disposed between the fibrous holding layer and each of the water-permeable layer and gas-permeable layer. In this regard, each of the water-permeable layer and the gas-permeable layer may comprise an adhesive bonding layer, which meets one of the other layers to combine and form the device. Additionally, the fibrous holding layer comprises a plurality of holes (134) such that the water-permeable layer and gas-permeable layer meet at each of the plurality of holes to form an overlapping junction (141). An aperture (142) extends through the water-permeable layer and gas-permeable layer at each of the overlapping junctions, wherein each aperture is configured to communicate exudate from a treatment site. Furthermore, the water-permeable layer comprises perforations (111) configured to communicate water therethrough.

The fibrous holding layer (130) further comprises a gas-donor composition (133) whereby upon contact from water or other activation fluid, the gas-donor composition is configured to release a therapeutic gas such as NO, $O_2$, $CO_2$, $H_2S$, $H_2$, CO or other gases known to one having skill in the art to provide therapeutic benefits to a subject.

Example 2—Second Illustrated Embodiment

Figure 3:
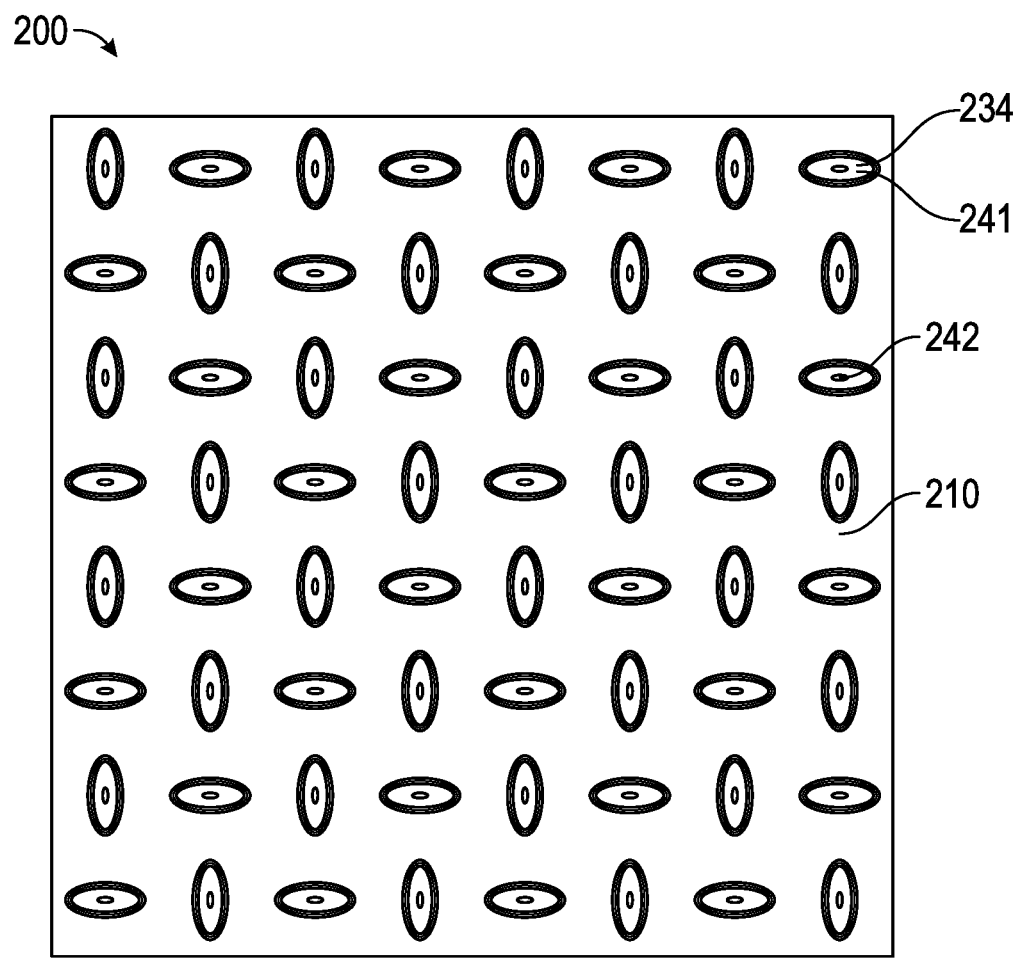
FIG. 3 shows a top view of a device in accordance with a second illustrated embodiment.

FIG. 3 shows a top view of a device (200) in accordance with a second illustrated embodiment. The device comprises a water-permeable layer (210) disposed on a fibrous holding layer (not shown). The fibrous holding layer includes a plurality of holes (234) wherein the water-permeable layer and a gas-permeable layer (not shown) are capable of forming an overlapping junction (241) at each of the plurality of holes. An aperture (242) extends through the water-permeable layer and gas-permeable layer to allow a subject's skin to breath during use of the device. The aperture can allow exudate to be expose. A therapeutic gas of interest is delivered across the device and presented to tissue cells.

As shown, the water-permeable layer (210) does not comprise any perforations. Instead, the water-permeable layer comprises a permeability coefficient that allows water to pass through at a desirable rate. A water-permeable layer that has excessive permeability will likely communicate too much water into the fibrous holding layer, or communicate water too quickly, and/or may release too much therapeutic gas thereby exhausting the source and limiting the duration of therapeutic effectiveness; whereas a water-permeable layer that has insufficient permeability may not communicate enough moisture into the fibrous holding layer required to produce the desired level of therapeutic gas from the gas donor composition, and/or may inhibit transfer of therapeutic gas through the gas-permeable layer to a delivery site. Permeability will be largely dependent on the type of device, the gas-donor composition and the particular application; however, will be generally in the range of 40 to 55000 Barrers. One having skill in the art will recognize standard conventional methods for modulating permeability of the water-permeable layer, such as selecting from available materials based on permeability factors, cross-linking, among other things, to achieve the desired level of passive therapeutic gas transport through the gas-permeable layer.

The overlapping junctions (241) are arranged on the device (200) such that each overlapping junction is oriented perpendicular to each adjacent overlapping junction.

Figure 4:
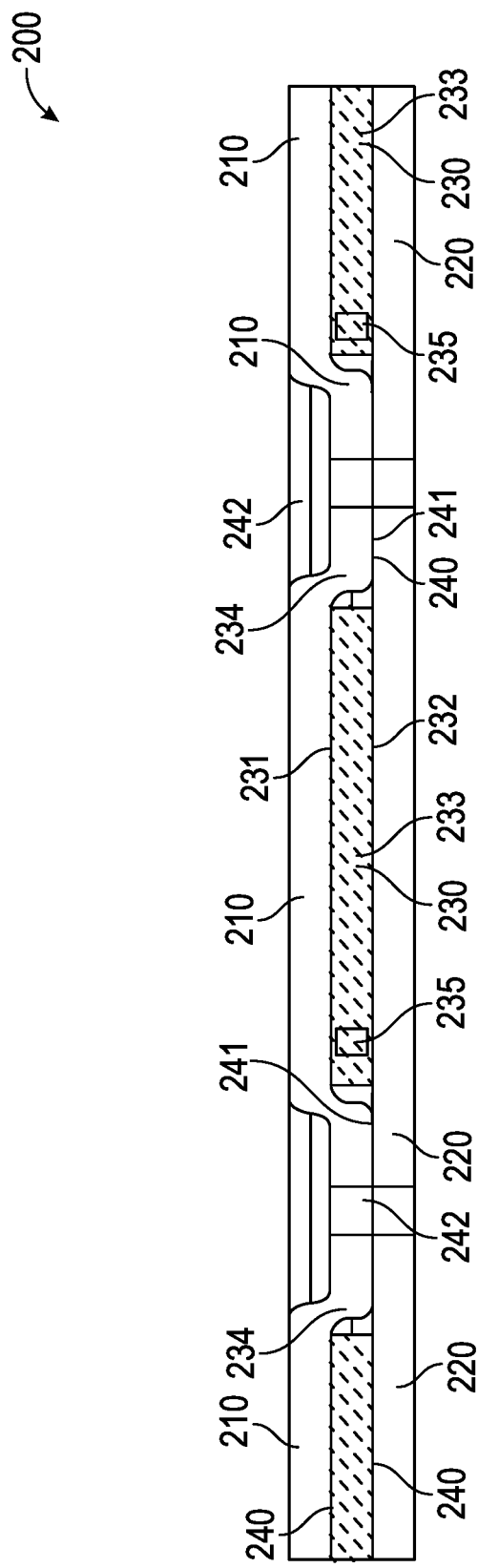
FIG. 4 shows a cross-sectional side view of the device according to the second illustrated embodiment.

FIG. 4 shows a cross-sectional side view of the device (200) according to the second illustrated embodiment. The device comprises a water-permeable layer (210) coupled to a first side (231) of a fibrous holding layer (230) by a first bonding layer (240a). Additionally, a gas-permeable layer (220) is coupled to a second side (232) opposite the first side by a second bonding layer (240b). The gas-permeable layer and water-permeable layer are further coupled to each other at each of a plurality of holes (234) extending through the fibrous holding layer. At each of the plurality of holes, the coupling of the water-permeable layer and gas-permeable creates an overlapping junction (241). Each of the overlapping junctions includes an aperture (242) extending therethrough which can allow exudate to pass through the device.

The fibrous holding layer (230) includes a gas-donor composition (233) embedded therein, and is configured to receive water from the water-permeable layer (210). Upon water contacting the gas-donor composition, a therapeutic gas is created, and then released through the gas-permeable layer to a treatment site. The gas-permeable layer (220) therefore contacts the treatment site and the water-permeable layer faces in an opposite direction from the treatment site.

The fibrous holding material (230) is shown further comprising one or more optional scavengers (235), wherein each of the scavengers is adapted to capture and remove gas byproducts before the gas products are able to make contact with the subject or otherwise escape the device. Examples of gas byproducts may include $NO_2$, $O_3$, and/or other potentially toxic gases. The scavenger may comprise $CA(OH)_2$, $Mg(OH)_2$, NaOH, CaO, soda lime, noXon, zeolite, or combinations thereof.

Generally, each of the scavengers (235) is coupled to at least a portion of the fibrous holding layer (230) and subsequently to the gas-donor composition (233) embedded therein. As shown, each of the scavengers is embedded within the fibrous holding material near one of the plurality of holes (234). However, there are a myriad of other configurations where the scavenger can be disposed including between the fibrous holding layer and water-permeable layer, between the fibrous holding layer and the gas-permeable layer, embedded within the fibrous holding layer, or any other configuration that can be appreciated by one having skill in the art. One means of embedding scavengers within the device (200) includes inserting the scavengers into the fibrous holding layer prior to attachment of the gas-permeable layer (220) and water-permeable layer (210). The scavengers can be spread across and pressed within the fibrous holding layer for a distributed coverage.

Example 3—Third Illustrated Embodiment

Figure 5:
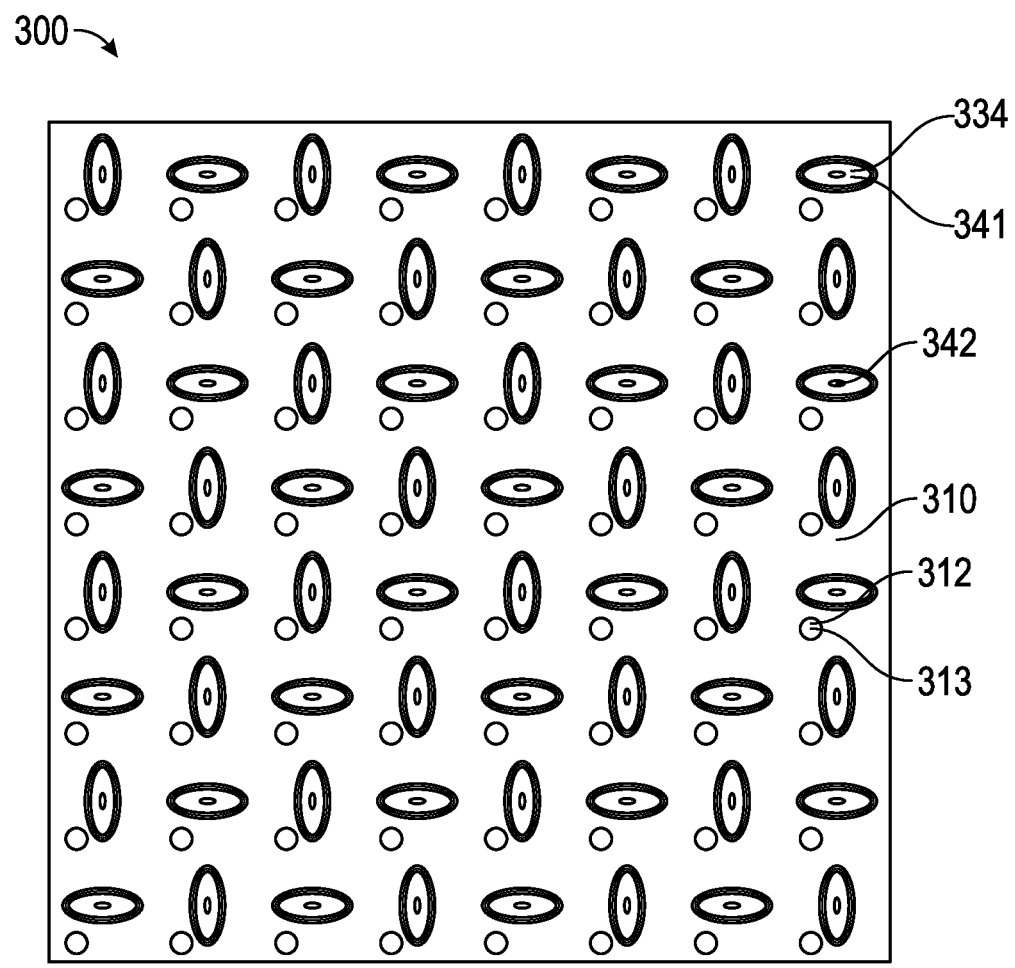
FIG. 5 shows a top view of a device in accordance with a third illustrated embodiment.

FIG. 5 shows a top view of a device (300) in accordance with a third illustrated embodiment. The device comprises a fibrous holding layer (not shown) coupled to a water-permeable layer (310) on one side and further coupled to a gas-permeable layer (not shown) on an opposite side. The device includes an array of overlapping junctions (341) caused by a meeting between the water-permeable layer and gas-permeable layer through a plurality of holes (334) which extends through the fibrous holding material. When the fibrous holding material is sandwiched between the water-permeable layer and gas-permeable layer, the plurality of holes causes the water-permeable layer, gas-permeable layer, or both to depress towards the fibrous holding layer and overlapping junctions. The device further comprises a blister-container (312) having an outer layer (313) and inner layer (not shown), wherein the blister layer is configured to release an amount of water upon sufficient force applied thereto. The amount of water is configured to travel to the fibrous holding layer and contact a gas-donor composition (not shown) embedded therein.

Figure 6:
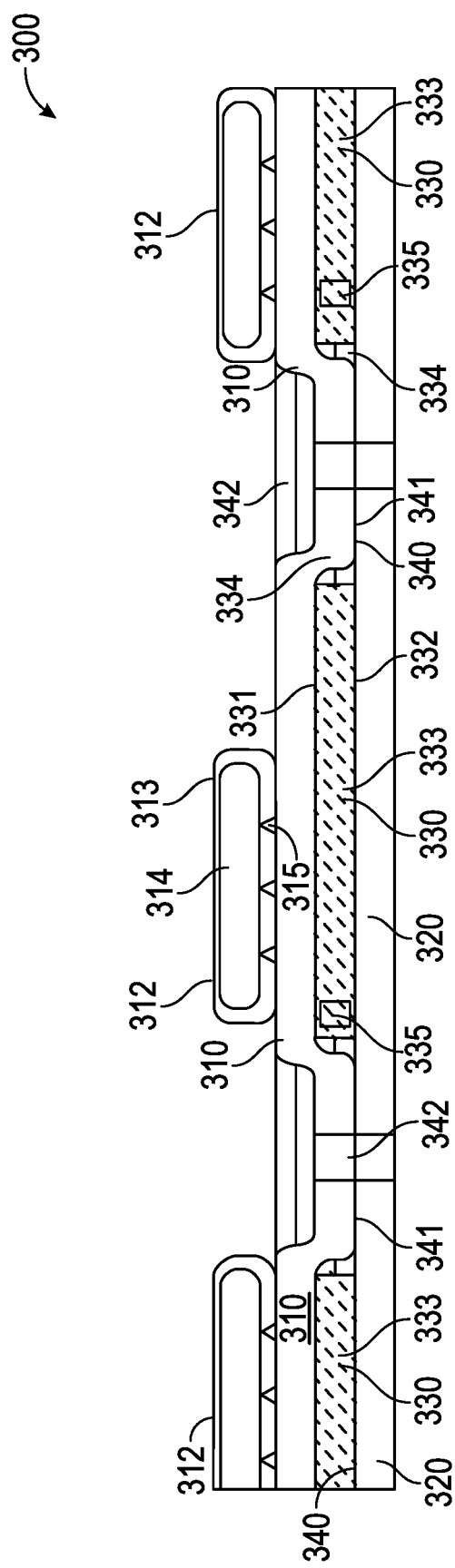
FIG. 6 shows a cross-sectional side view of the device according to the third illustrated embodiment.

FIG. 6 shows a cross-sectional side view of the device (300) according to the third illustrated embodiment. The device comprises a fibrous holding layer (330) disposed between a water-permeable layer (310) and a gas-permeable layer (320). The fibrous holding layer comprises a first side (331), and a second side (332) opposite the first side, wherein the water-permeable layer is coupled to the first side and the gas-permeable layer is coupled to the second side. The fibrous holding layer further comprises a gas-donor composition (333) embedded therein in addition to one or more scavengers (335) coupled to at least a portion of the fibrous holding layer. A plurality of holes (334) is each disposed in the fibrous holding layer, which causes the water-permeable layer and gas-permeable layer to form an overlapping junction within each of the plurality of holes. Each of the overlapping junctions comprises an aperture (342) extending therethrough.

The device (300) further comprises one or more blister-containers (312) wherein each of the blister-containers comprises an outer layer (313) and an inner layer (314). A volume of the blister-container, between the outer and inner layers, comprises an amount of water and is sealed at a periphery of the outer and inner layers. The blister-container further comprises one or more puncture elements (315) such that upon a sufficient force, the amount of water encapsulated by the blister-container is released and configured to travel to the fibrous holding layer (330) for activation of the gas-donor composition (333). While FIG. 6 shows the puncture elements in a particular orientation, it should be recognized that the puncture elements may be attached to the outer layer of the blister-container pointing downward for puncturing the inner layer thereof, or any other structural modification that achieves the result of releasing water from the blister-container to contact the fibrous holding layer and gas donor composition therein. The one or more blister-containers can be disposed in various positions of the device including on top of the water-permeable layer (310), integrated within the water-permeable layer, or disposed between the water-permeable layer and the fibrous holding layer. In some embodiments, the amount of water released from the blister-container permeates through the water-permeable layer. In other embodiments, the blister-container further comprises a one-way delivery valve coupled to the fibrous holding layer and configured to communicate the amount of water therethrough.

As shown, the device (300) may comprise a plurality of blister-containers (312) disposed between apertures (342) so as to avoid interference of said apertures. In other embodiments, the device comprises a single blister-container forming a layer which further comprises a plurality of openings similar to the plurality of holes (334) of the fibrous holding layer (330) so as to allow the apertures to operate effectively.

Example 4—Method of Making

In one example, a paper material is provided as the fibrous holding layer. A gas-donor material, such as SNAP (releases nitric oxide gas), is dissolved in a solvent, for example, alcohol, to form a solution. The paper material is soaked with the solution, and the alcohol is evaporated during drying. The result is a paper material with an NO donor material embedded therein. Holes are cut through the paper material, preferably with a laser cutting instrument. The water-permeable layer and gas-permeable layer are then attached to the paper, preferably by an adhesive layer therebetween. Apertures may be cut through the overlapping junctions (areas where water-permeable layer and gas-permeable layer meet at the holes), again this is preferably achieved using a laser cutting instrument. The device is cut to size and packaged in a water-tight container or pouch, optionally with a desiccant.

During manufacturing of the device, the perforations are generally cut into the water-permeable layer prior to the water-permeable layer coupling with the fibrous holding layer, thereby preventing accidental activation of the gas-donor composition due to photons from a laser cutter.

INDUSTRIAL APPLICABILITY

The invention may be practiced in various embodiments to provide a device, such as a pad, that is configured to provide a therapeutic gas rich environment to a treatment site to promote healing, reduce fibrosis and scar formations while maintaining anti0inflammatory, anti-thrombotic, anti-microbial, and vasodilating properties.

The device may be used for acne, skin blemishes, and other cosmetic related ailments and applications. Additionally, the device can be used for wound healing and other medical applications. One with skill in the art upon a reading of the disclosure will appreciate a myriad of other uses for the device.

The device can be used for long and prolonged therapeutic or non-therapeutic treatments that require a release of a therapeutic gas to tissue cells. The device can also be used for short durations but with high therapeutic gas dosage treatment.

Additionally, methods for manufacturing the device are disclosed. As such, the invention is applicable to products and methods of manufacture.

REFERENCE SIGNS LIST device (100; 200; 300)
water-permeable layer (110; 210; 310)
perforation (111)
gas-permeable layer (120; 220; 320)
fibrous holding layer (130; 230; 330)
first side (131; 231; 331)

second side (132; 232; 332)
gas-donor composition (133; 233; 333)
hole (134; 234; 334)
scavenger (235; 335)
bonding layer (140; 340)
overlapping junction (141; 241; 341)
aperture (142; 242; 342)
first bonding layer (240a)
second bonding layer (240b)
blister-container (312)
outer layer (313)
inner layer (314)
puncture element (315)

What is claimed is:

1. A device for providing therapeutic gas to a subject at a treatment site, the device comprising:
a water-permeable layer;
a gas-permeable layer; and
a fibrous holding layer disposed between each of the water-permeable layer and the gas-permeable layer, the fibrous holding layer comprising a gas-donor composition embedded therein;
wherein:
the gas-donor composition is one that emits therapeutic gas upon contact with water, and
the device is adapted to direct the therapeutic gas emitted therefrom toward the treatment site;
wherein each of the water-permeable layer and the gas-permeable layer further comprises a bonding layer on a surface thereof; and
further wherein the fibrous holding layer comprises a plurality of holes, and the water-permeable layer and the gas-permeable layer are bonded together at each of the plurality of holes by the bonding layer to form a plurality of overlapping junctions.

2. The device of claim 1, wherein one or more of the overlapping junctions comprises an aperture extending therethrough, the aperture configured to communicate exudate from the treatment site.

3. The device of claim 2, wherein each of the plurality of holes and corresponding overlapping junctions are oval-shaped.

4. The device of claim 3, wherein a first of the plurality of oval-shaped junctions is oriented perpendicular with an adjacent second junction.

5. The device of claim 2, wherein the water-permeable layer comprises a plurality of perforations.

6. The device of claim 1, wherein the water-permeable layer comprises glass, polymers, hydrophilic materials, cellulose, polyglucose, polyacrylonitrile, polykeratin, polydimethylsiloxane, polyester, polyurethane, polyfibrin, xerogel, silicone, alginate, collagen, foams, hydrocolloid, hydrogels, polyglucose, lauryl polyglucose, polydimethylsiloxane, polyacrylate, polyacrylonitrile, polykeratin, siloxane, poly(lactic-co-glycolic acid), neoprene, sorbothane, polychloroprene, polyamide, polyimide, polyethylene glycol, polypropylene oxide, polymethlyacrylate, polyvinyl, polydextrin, alginate, polyisobutylene tackifiers, carboxymethyl cellulose, alginate, gelatin, agarose, polyolefin copolymer, polyether block amide, polyethylene, Nylon, polyethylene terephthalate, or a combination thereof.

7. The device of claim 1, wherein the fibrous holding layer comprises cellulose, fabric, polyglucose, polyacrylonitrile, polykeratin, polydimethylsiloxane, polyester, polyurethane, polyfibrin, poly-para-phenylene terephthalamide, cotton, flax, hemp, or a combination thereof and the gas-donor composition embedded therein.

8. The device of claim 1, wherein the gas-donor composition is selected from the group consisting of: diazeniumdiolated diamine, S-nitroso-albumin, S-nitroso-N penicillamine (SNAP), S-nistrosocystine (CysNO), S-nitrosoglutathione (GSNO), diazeniumdiolated dibutylhexyldiamine (DBHD N2O2), Diethylenetriamine/NO adduct (DEAT/NO), Diethylamine NONOate (DEA/NO), Dipropylenetriamine NONOate (DPTA/NO), 6-(2-Hydroxy-1-methyl-2-nitrosohydrazino)-N-methyl-1-hexanamine (MAHMA/NO), S-nitroso-N-acetylpenicillamine, a polymer possessing an appended SNAP species, or a combination thereof.

9. The device of claim 1, wherein the therapeutic gas comprises: NO, $O_2$, $CO_2$, $H_2S$, $H_2$, or CO.

10. The device of claim 1, wherein the gas-permeable layer comprises polymer, hydrophilic materials, cellulose, polyglucose, polyacrylonitrile, polykeratin, polydimethylsiloxane, polyester, polyurethane, polyfibrin, xerogel, silicone, alginate, collagen, foams, hydrocolloid, hydrogels, polyglucose, lauryl polyglucose, polydimethylsiloxane, polyacrylonitrile, polykeratin, siloxane, poly(lactic-co-glycolic acid), neoprene, sorbothane, polychloroprene, polyamide, polyimide, polyethylene glycol, polypropylene oxide, polymethlyacrylate, polyvinyl, polydextrin, alginate, polyisobutylene tackifiers, carboxymethyl cellulose, alginate, gelatin, agarose, polyolefin copolymer, polyether block amide, polyethylene, Nylon, polyethylene terephthalate or a combination thereof.

11. The device of claim 1, further comprising one or a plurality of scavengers embedded in the fibrous holding layer, each of the scavengers being adapted to capture and remove gas byproducts.

12. The device of claim 1, wherein the water-permeable layer comprises a blister-layer, the blister-layer comprising an outer layer and an inner layer sealed at a periphery thereof and encapsulating a volume of water therein, the outer layer configured with one or more puncture elements for puncturing the inner layer upon receiving a puncturing force and for releasing the volume of water therethrough.

13. The device of claim 1, wherein the fibrous holding layer is devoid of water.

14. The device of claim 1, wherein the gas-donor composition comprises an inactive state.

15. A method of making a device for providing therapeutic gas to a subject at a treatment site, the method comprising:
dissolving a therapeutic gas donor material in a solvent to form a solution;
soaking a fibrous holding layer in the solution;
evaporating the solvent from the fibrous holding layer to leave the therapeutic gas donor material embedded therein;
cutting a plurality of holes in the fibrous holding layer;
applying a water-permeable layer to the fibrous holding layer at a first side thereof;
applying a gas-permeable layer to the fibrous holding layer at a second side thereof opposite the first side;
applying a force to sandwich the combination of said layers, the force creating overlapping junctions where the water-permeable layer and the gas-permeable layer meet at the holes of the fibrous holding layer; and
cutting a plurality of apertures, each of the plurality of apertures being independently disposed at one of the overlapping junctions.

16. The method of claim 15, wherein said cutting the holes or cutting the apertures is performed using a laser cutting instrument.

17. The method of claim 15, wherein the solvent comprises an alcohol.

18. The method of claim 15, further comprising: cutting perforations in the water-permeable layer.

* * * * *